US011796524B1

(12) United States Patent
Ross et al.

(10) Patent No.: US 11,796,524 B1
(45) Date of Patent: Oct. 24, 2023

(54) SYSTEMS AND METHODS FOR PROCESSING AIR PARTICULATE DATASETS

(71) Applicant: MASSACHUSETTS MUTUAL LIFE INSURANCE COMPANY, Springfield, MA (US)

(72) Inventors: Gareth Ross, Amherst, MA (US); Sears Merritt, Groton, MA (US)

(73) Assignee: Massachusetts Mutual Life Insurance Company, Springfield, MA (US)

( * ) Notice: Subject to any disclaimer, the term of this patent is extended or adjusted under 35 U.S.C. 154(b) by 1064 days.

(21) Appl. No.: 16/263,741

(22) Filed: Jan. 31, 2019

Related U.S. Application Data (60) Provisional application No. 62/625,241, filed on Feb. 1, 2018.

(51) Int. Cl.
| | |
|---|---|
| *G06Q 40/08* | (2012.01) |
| *G06N 3/02* | (2006.01) |
| *G06F 16/9035* | (2019.01) |
| *G06F 16/909* | (2019.01) |
| *G01N 33/00* | (2006.01) |
| *G01N 1/22* | (2006.01) |
| *G06F 16/9038* | (2019.01) |
| *G06Q 30/0283* | (2023.01) |

(52) U.S. Cl.
CPC ....... *G01N 33/0034* (2013.01); *G01N 1/2273* (2013.01); *G06F 16/909* (2019.01); *G06F 16/9035* (2019.01); *G06F 16/9038* (2019.01); *G06N 3/02* (2013.01); *G06Q 30/0283* (2013.01); *G06Q 40/08* (2013.01); *G01N 2001/2276* (2013.01)

(58) Field of Classification Search
None
See application file for complete search history.

(56) References Cited

U.S. PATENT DOCUMENTS

| | | | | |
|---|---|---|---|---|
| 7,389,158 | B2 * | 6/2008 | Desrochers | G01N 33/0034 700/277 |
| 10,139,384 | B1 * | 11/2018 | Nourbakhsh | G01N 33/0075 |
| 10,222,360 | B1 * | 3/2019 | Nourbakhsh | G01N 33/0075 |
| 10,553,321 | B2 * | 2/2020 | Hayward | G06F 3/04842 |
| 10,725,008 | B2 * | 7/2020 | Dong | G01N 35/00871 |
| 10,752,008 | B2 * | 8/2020 | Shimizu | B41J 2/175 |
| 11,340,097 | B1 * | 5/2022 | Deutsch | G08B 29/188 |
| 11,488,069 | B2 * | 11/2022 | Kuo | G06N 3/08 |

(Continued)

OTHER PUBLICATIONS

S. F. Mihalache, M. Popescu and M. Oprea, "Particulate matter prediction using ANFIS modelling techniques," 2015 19th International Conference on System Theory, Control and Computing (ICSTCC), 2015, pp. 895-900. (Year: 2015).*

(Continued)

*Primary Examiner* — Mohammad Z Shaikh
(74) *Attorney, Agent, or Firm* — Foley & Lardner LLP (57) ABSTRACT

Disclosed is a method and a system for efficiently and accurately processing air particulate datasets when facing a high number of air particulate datasets from multiple locations to generate an artificial intelligence model having one or more computer-based rules that determines eligibility of a user to avail a health-related service based on air particulate records associated with current and past locations of the user.

20 Claims, 3 Drawing Sheets

(56) References Cited

U.S. PATENT DOCUMENTS

| | | | | |
|---|---|---|---|---|
| 2006/0173580 A1* | 8/2006 | Desrochers | ........ | G01N 33/0075 73/31.01 |
| 2015/0117767 A1* | 4/2015 | Gong | ...................... | G06F 18/00 382/160 |
| 2016/0314256 A1* | 10/2016 | Su | .......................... | G16H 50/50 |
| 2018/0073759 A1* | 3/2018 | Zhang | ..................... | F24F 11/30 |
| 2018/0321208 A1* | 11/2018 | Bai | ........................ | G06N 20/00 |
| 2018/0325422 A1* | 11/2018 | Sokol | ....................... | A62B 7/10 |
| 2018/0340701 A1* | 11/2018 | Baughman | ......... | G01N 33/0036 |
| 2019/0033278 A1* | 1/2019 | Mou | ...................... | G08B 21/12 |
| 2019/0080801 A1* | 3/2019 | Klos | ..................... | G16H 40/60 |
| 2019/0325334 A1* | 10/2019 | Kuo | ...................... | G08B 21/12 |

OTHER PUBLICATIONS

D. B. Neill, "New Directions in Artificial Intelligence for Public Health Surveillance," in IEEE Intelligent Systems, vol. 27, No. 1, pp. 56-59, Jan.-Feb. 2012. (Year: 2012).*

* cited by examiner

SYSTEMS AND METHODS FOR PROCESSING AIR PARTICULATE DATASETS

CROSS-REFERENCE TO RELATED APPLICATIONS

This application claims priority to U.S. Provisional Patent Application Ser. No. 62/625,241, filed on Feb. 1, 2018, which is hereby incorporated by reference in its entirety.

This application is also related to U.S. Provisional Patent Application Ser. No. 62/597,824, filed on Dec. 12, 2017 and U.S. Non-Provisional patent application Ser. No. 16/216,770, filed on Dec. 11, 2018, all of which are incorporated herein in their entirety.

TECHNICAL FIELD

This application generally relates to data processing systems, and more specifically relates to methods and systems for generating and processing air particulate datasets.

BACKGROUND

Many industrial activities produce pollution of one or more types. Examples of the pollution include carbon dioxide emissions, greenhouse gases, noise pollution, light pollution, consumer waste pollution, and any combinations thereof. Several organizations collect pollutant data in various cities around the world in order to quantify and analyze the pollutant data, which result from human and industrial activity, due to the increasing concern of the negative impact of the pollution on the human health and environment.

In China, several organizations have collected pollutant data for approximately last 40 years. The organizations made use of approximately 42,000 pollutant data collectors all across China over a period of 40 years because of which the monitored and collected air particulate datasets are now available for almost all Chinese provinces and municipalities, with some provinces containing multiple data points from a few cities and air monitoring stations. The thousands of pollutant data collectors report big air particulate datasets having concentrations in (mg/m3) for major pollutants such as sulfur dioxide ($SO_2$), nitrogen dioxide ($NO_2$), and particulate matter (PM10, particles with a diameter of 10 microns or less) in real-time, hourly basis.

Various problems occur in connection with management and processing of the big pollutant datasets, using conventional technologies, since the pollutant datasets are so large and complex that the pollutant datasets become difficult to work with using on-hand management and analytical tools. In particular, the processing of the larger pollutant datasets for any management application may cause problems involving access times, processing costs, and load balancing requirements among multiple pollutant data collector centers that are geographically dispersed, and subject to varying levels of access demands depending on particular locations and/or particular times.

SUMMARY

What is therefore needed is a method and a system that efficiently and effectively manages and processes distributed big pollutant datasets generated across multiple sites at real-time for an application. The processed big pollutant datasets may be used as an input to generate an artificial intelligence model, such as a mortality model, which may be executed to determine eligibility of a user to avail a health-related service. When facing a high number of big pollutant datasets from multiple sites, a computer-specific set of rules may also be applied to the mortality model to produce efficient and accurate results for each user.

In one embodiment, a server-implemented method may include receiving, by a server programmed according to an event-driven asynchronous architecture, from a client computing device operated by a user, a request from an input field of a network page served to the client computing device, the request comprising one or more attributes of the user, a list of locations, and a time period during which the user has been associated with each location; in response to receiving the request, querying, by the server, an application server to receive a set of air particulate datasets corresponding to the user, wherein each set of air particulate datasets comprises air particulate data associated with at least one location within the list of locations and a corresponding time period; generating, by the server, a multi-dimensional feature vector where each dimension corresponds to a location from the list of locations and the corresponding time period at which the user is associated with the location; retrieving, by the server, one or more artificial intelligence models in accordance with the multi-dimensional feature vector, each artificial intelligence model having a neural network that incorporates air particulate data; executing, by the server, the one or more artificial intelligence models based on the multi-dimensional feature vector and the set of air particulate datasets; generating, by the server executing the one or more artificial intelligence models, an indicator corresponding to an output of the one or more artificial intelligence models; and upon the indicator satisfying a threshold, executing, by the server, a pricing model module.

In another embodiment, a system may include a network, a client computing device operated by a client, and a server programmed according to an event-driven asynchronous architecture. The server is configured to receive from the client computing device a request from an input field of a network page served to the client computing device, the request comprising one or more attributes of the user, a list of locations, and a time period during which the user has been associated with each location; query an application server to receive a set of air particulate datasets corresponding to the user, wherein each set of air particulate datasets comprises air particulate data associated with at least one location within the list of locations and a corresponding time period; generate a multi-dimensional feature vector where each dimension corresponds to a location from the list of locations and the corresponding time period at which the user is associated with the location; retrieve one or more artificial intelligence models in accordance with the multi-dimensional feature vector, each artificial intelligence model having a neural network that incorporates air particulate data; execute the one or more artificial intelligence models based on the multi-dimensional feature vector and the set of air particulate datasets; generate an indicator corresponding to an output of the one or more artificial intelligence models; and upon the indicator satisfying a threshold, execute a pricing model module.

It is to be understood that both the foregoing general description and the following detailed description are explanatory and are intended to provide further explanation of the subject matter as claimed.

BRIEF DESCRIPTION OF THE DRAWINGS

The accompanying drawings constitute a part of this specification and illustrate an embodiment of the subject matter and together with the specification, explain the subject matter.

DETAILED DESCRIPTION

Reference will now be made to the embodiments illustrated in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one ordinarily skilled in the relevant art and having possession of this disclosure, are to be considered within the scope of the subject matter disclosed herein. The present disclosure is here described in detail with reference to embodiments illustrated in the drawings, which form a part here. Other embodiments may be used and/or other changes may be made without departing from the spirit or scope of the present disclosure. The embodiments described in the detailed description are not meant to be limiting of the subject matter presented here.

A server may serve a network page to a client user operating a client computing device. The network page may include a set of fields programmed to receive a plurality of inputs from the client user, such as a plurality of alphanumeric strings or a plurality of binary values. The network page may be programmed to submit the inputs to the server, such as when the fields are populated or when triggered via the client user. For example, a webserver may serve a webpage to a smartphone. The webpage is programmed to receive a set of user inputs from the smartphone of the client user, such as personal information, address, health information, a list of geographical locations where the client user have lived. Upon receiving the inputs from the client computing device, the server may create a user profile based on information parsed from the inputs. The user profile may include information about air particulate datasets and big pollutant datasets in the geographical locations during the time period the user lived in the geographical locations. The server may then execute machine-learning algorithms to process the information associated with the user profile, and determine eligibility of the client user to avail a health-related service. The server may then provide an output to the client computing device based on processing the user profile. The output may be published on a user interface of the client computing device.

As described herein, various disclosed technologies can be implemented via a plurality of computers (servers/clients) utilizing a plurality of data structures/messages. The implementations include data structure/message generation/formation, storage, retrieval, population, copying, moving, editing, modifying, sorting, searching, sending, receiving, updating, deleting, encrypting, decrypting, de-duplicating, converting, uploading, downloading, or any other local or network-based data structure/message operation associated with a structure/message (data shell) or the data itself (content). For example, the structure/message (shell) can comprise a file, a table, a spreadsheet, an array, a matrix, a linked list, a tree, a string, a quadtree, a stack, a deck, or any other structures of datasets. The datasets may contain any alphanumeric, image, acoustic, binary, symbolic, equation, formula, or any other content. Also, note that various disclosed algorithms are some non-limiting examples and other variations are possible.

Figure 1:
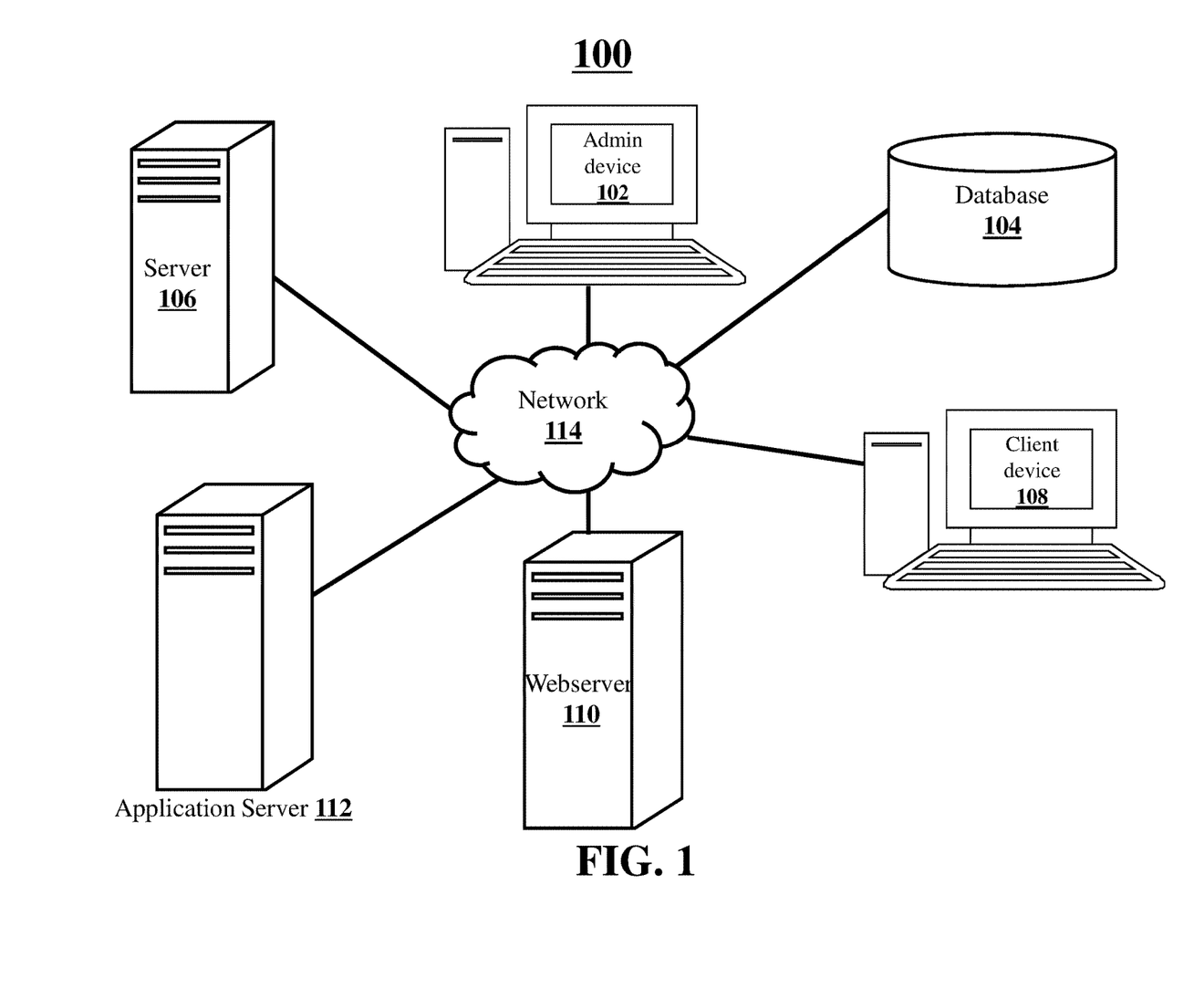
FIG. 1 shows components of a computer-based mortality model management system, according to an embodiment.

FIG. 1 shows components of a computer-based mortality model management system 100. The system 100 may provide recommendations of market based health-related services to a client (also known as a user or a customer). The system 100 may include a computer interface and a communications link, via which administrators of the system 100 may provide to the clients recommendations of the market based health-related services, in response to comprehensive analysis of indicators associated with a big collection of air particulate datasets, corresponding to each of the past and current geographical locations of user's residence and office.

The system 100 may include an administrator device 102 operated by administrators, a database 104, a server 106, a client device 108, a web server 110, and an application server 112. The administrator device 102, the database 104, the server 106, the client device 108, the web server 110, and the application server 112 are connected through a network 114. The examples of the network 114 include, but are not limited to, private or public LAN, WLAN, MAN, WAN, and the Internet. The network 114 can include both wired and wireless communications according to one or more standards and/or via one or more transport mediums. The communication over the network 114 may be performed in accordance with various communication protocols such as Transmission Control Protocol and Internet Protocol (TCP/IP), User Datagram Protocol (UDP), and IEEE communication protocols. In one example, the network 114 may include wireless communications according to Bluetooth specification sets, or another standard or proprietary wireless communication protocol. The network 114 may also include communications over a cellular network, including, e.g. a GSM (Global System for Mobile Communications), CDMA (Code Division Multiple Access), EDGE (Enhanced Data for Global Evolution) network.

The system 100 is described in the context of computer-executable instructions, such as program modules, being executed by a server computer, such as the server 106. The program modules may include programs, objects, components, and data structures that perform particular tasks or implement particular abstract data types. The features of the system 100 may be practiced either in a server computing device or in a distributed server computing environment where tasks are performed by remote processing devices that are linked through the communications network 114. In a distributed server computing environment, the program modules may be located in both local and remote server computer storage media including memory storage devices.

The system 100 is based on a distributed network operation model, which allocates tasks/workloads between various servers, which provide a resource/service, and clients, which request the resource/service. Although the servers and the clients illustrate different computers/applications, in some embodiments, the servers and the clients reside in, share, or are one system/application. Further, the system 100 entails allocating a large number of resources to a small number of servers, where complexity of the clients, depends on how much computation is offloaded to the small number of servers, i.e., more computation offloaded from the clients onto the servers leads to lighter clients, such as being more reliant on network sources and less reliant on local computing resources. However, note that other computing models are possible as well. For example, such models can comprise decentralized computing, such as peer-to-peer (P2P), for instance Bit-Torrent, or distributed computing, such as via a computer cluster where a set of networked computers works together such that the computer can be viewed as a single system.

Each component of the system 100 is implemented in a logic, whether hardware-based or software-based. For example, when the logic is hardware-based, then such logic can comprise circuitry, such as processors, memory, input devices, output devices, or other hardware, that is configured, such as via programming or design, to implement a functionality of a respective component. Likewise, when the logic is software-based, then such logic can comprise one or more instructions, such as assembly code, machine code, object code, source code, or any other type of instructions, which when executed, such as via running or compilation, implement a functionality of a respective component.

In operation, in response to a receipt, by the server 106, over the network 114, of an input from an input field of a network page served to the client device 108 of the user over the network 114, a request, by the server 106, is placed for a numeric value from the application server 112 based on the input. Further, based on the input, the application server 112 queries a plurality of databases 104, which may be remote to the server 106, and correspondingly receives a plurality of query results from the databases 104. Then, the application server 112 submits the query results to an application-programming interface hosted on the application server 112 and receives a feature vector from the application-programming interface.

The feature vector maybe a vector that contains information describing important characteristics of information associated with a user. The feature vector maybe an n-dimensional vector of numerical features that represent information associated with the user. The information may include air particulate data corresponding to each of past and current geographical location of the user. The application server 112 may dynamically retrieve an artificial intelligence model, based on the value of the feature vector, from a model record of an in-memory database hosted on a database server associated with the database 104. Subsequently, the application server 112 submits the feature vector into the model running on an application of the application server 112. In response, the application server 112 receives the numeric value from the model. Accordingly, the numeric value is sent to the server 106, which dynamically updates the network page to the client device 108 based on the numeric value.

An application server 112 may host a software application, and a set of business logic for the software application. Therefore, as instructed by the software application, the application server 112 can communicably interface with the server 106 through a firewall and the database 104. For example, the application server 112 can act as a middle-tier server, with the server 106 acting as front-tier server, and a database server associated the database 104 acting as a back-end server. For example, the application server 112 can comprise an IBM WebSphere application server or a SAP Web application server. In some embodiments, where the firewall is lacking, then the application server 112 can still communicably interface with the server 106, which may be directly.

The application server 112 may comprise a plurality of independent cores, such as a multicore processor comprising a computing component with two or more independent processing units, which are the units that read and execute program instructions, such as via multiprocessing or multithreading. The instructions are processing instructions, such as add, move data, or branch, but the cores can run multiple instructions concurrently, thereby increasing an overall operational speed for the software application, which is amenable to parallel computing. The cores can process in parallel when concurrently accessing a file or any other data structure, as disclosed herein, while being compliant with atomicity, consistency, isolation, and durability (ACID) principles, which ensure that such data structure operations/transactions, such as read, write, erase, or others, are processed reliably, such as for data security or data integrity. For example, a data structure can be accessed, such as read or written, via at least two cores concurrently, where each of the cores concurrently processes a distinct data structure record or a distinct set of data such that at least two data structure records or at least two sets of the data are processed concurrently, without locking the data structure between such cores. However, note that data locking is possible. Note that there can be at least two cores, such as two cores, three cores, four cores, six cores, eight cores, ten cores, twelve cores, or more. The cores may or may not share caches, and the cores may or may not implement message passing or shared-memory inter-core communication methods. The network topologies to interconnect cores may include bus, ring, two-dimensional mesh, and crossbar. Homogeneous multi-core systems include only identical cores, heterogeneous multi-core systems can have cores that are not identical. The cores in multi-core systems may implement architectures, such as very long instruction word (VLIW), superscalar, vector, or multithreading. In some embodiments, whether additionally or alternatively, in whole or in part, at least one of the server 106, the database server associated with the database 104, the administrative device 102, the webserver 110, or the client device 108 can comprise a plurality of independent cores, such as a multicore processor comprising a computing component with two or more independent processing units, which are the units that read and execute program instructions, such as via multiprocessing or multithreading, as disclosed herein. Such configurations may enable parallel processing of relevant information, as disclosed herein, such as when used via many users for various tasks disclosed herein and thereby efficiently increase system computational speed. For example, when processing hundreds of concurrent connections, then such parallel processing architecture enables handling these connections by a small number of multiplexing processing, such as via one process per core.

A webserver 110 may host a website accessible to end-users, where the content presented via the various webpages may be controlled. The webserver 110 may be any computing device comprising a processor and non-transitory machine-readable storage capable of executing the various tasks and processes described herein. Non-limiting examples of the computing devices may include workstation computers, laptop computers, server computers, laptop computers, and the like. While the system 100 includes a single webserver 110, the webserver 110 may include any number of computing devices operating in a distributed computing environment.

The webserver 110 may execute software applications configured to host a website, which may generate and serve various webpages to client device(s) 108. The website may be used to generate and access data stored on the database 104. In some implementations, the webserver 110 may be configured to require user authentication based upon a set of user authorization credentials e.g., username, password, biometric. In such implementations, the webserver 110 may access the database 104 configured to store user credentials, which the webserver 110 may be configured to reference in order to determine whether a set of entered credentials purportedly authenticating the user match an appropriate set of credentials that identify and authenticate the user. Similarly, in some implementations, the webserver 110 may generate and serve webpages to the client device 108 based upon a user role within the system 100. In such implementations, the user role may be defined by data fields in the user records stored in the database 104, and authentication of the user and the user role may be conducted by the webserver 110. The webserver 110 may then be instructed to generate webpage content, access health service planning tool stored in the database 104, according to the user profile defined by the user record in the database 104.

When a user accesses the system 100, the user most often does so using the client device 108 that is connected to the network 114. The network 114 is connected to the server 106. The user commonly accesses the server 106 through the Internet. The health service planning tool is available via an institution via the webserver 110. Once the user accesses the link to the health service planning tool to generate a request to avail one or more health related services, the server 106 informs the user of the information that the user will need to input, i.e., current and all past residence and work locations of the user, time-period during which the user lived in all past residence and work locations, monthly income, or amount of net worth, in order for the server 106 to determine eligibility of the user to avail any of the one or more health related services and/or provide a recommendation for a health-related service if the user is found to be eligible. The server 103 may provide links to indicate current and past location information, and a risk tolerance bar graph to assist the user in determining their level of health risk. Once the user begins the process, the server 106 takes the user through a series of screens related to, but not limited, to financial information and health objectives, where the user is asked a series of questions, i.e., what is your goal, income, and whether you are making tax-advantaged or taxable health related investments. Depending upon each of the locations the user have lived, the server 106 provides the user with a recommendation of a health-related service available to the user and corresponding costs.

A client device 108 is a client computing device allowing a user to interact with the server 106 via the webserver 110. The client device 108 may execute an Internet browser or local application that access the webserver 110 in order to issue requests or instructions to the server 106. The client device 108 may transmit credentials from user inputs to the webserver 110, from which the webserver 110 may authenticate the user. The client device 108 may comprise any number of input devices configured to receive any number of data inputs, including various types of data inputs allowing for authentication (e.g., username, passwords, certificates, and biometrics). The client device 108 may be any computing device comprising a processor and non-transitory machine-readable storage medium allowing the client device 108 to perform the various tasks and processes described herein.

As an example of the client device 108 operation, the client device 108 may execute an Internet browser that accesses the webserver 110 hosting a health service-planning website that allows for users to access to health-related services, and allows the managers to advertise health-related services to potential users. Using the client device 108, a user may select a health-related service in which to register. As the transaction proceeds, the client devices 108 of the user may be used to upload machine-readable computer files containing transaction information. The computer files may be stored into document records in the database 104. The client device 108 may issue queries or instructions to the server 106 via the webpages generated by the webserver 110, which then instruct the server 106 to perform various tasks, such as retrieving a health-related service from the database 104.

A plurality of databases 104 may store pollutant data for one or more countries. For instance, the database 104 may store a large amount of pollutant data obtained from approximately 42,000 pollutant data collectors all across China over a period of 40 years. The pollutant data collectors may be installed in air monitoring stations to collect air pollutant data in real-time. These pollutant data collectors may report big air particulate datasets having concentrations in (mg/m3) for major pollutants such as sulfur dioxide ($SO_2$), nitrogen dioxide ($NO_2$), and particulate matter (PM10, particles with a diameter of 10 microns or less) in real-time, hourly basis, and these datasets are then stored in the database 104.

The database 104 may store health service-planning tools. Each tool may accommodate a variety of goals, time horizons, and tolerances. The database 104 may also store datasets that are associated with several users, where the datasets each contain at least one field identifying which user account was associated with a particular data field. The database 104 may also store personal attributes and genetic data associated with each user such as name, user identifiers (e.g., Social Security numbers, driver's license number, or other identifiers), age, height, weight, and the like. The database 104 may further store datasets generated, stored, and/or received by the server 106. The database 104 may receive user attribute data from an electronic interaction with the users; for example, the server 106 may provide an online accessible graphical user interface configured to receive personal attributes associated with the user. The database 104 may also receive user attribute data from the webserver 110 and/or pollutant data for each city and county from a third-party server and/or one or more pollutant detection generating systems.

The databases 104 may be in communication with one or more internal and external databases via the network 114 and include a non-transitory machine-readable storage media capable of receiving, storing, updating polices, rule files, events, tasks, and other customer data. The databases 104 may have a logical construct of data files that are stored in non-transitory machine-readable storage media, such as a hard disk or memory, controlled by software modules of a database program (for example, SQL), and a related database management system (DBMS) that executes the code modules (for example, SQL scripts) for various data queries and other management functions generated by the subscriber server, event-generating/detecting devices such as a webserver, and/or any other devices of the system 100. In some embodiments, a memory of the databases 104 may be a non-volatile storage device for storing customer/user and health organization data and instructions, to be used by a processor of the server 106 and/or any other devices of the system 100 for processing and execution of the tasks. The memory of the databases 104 may be implemented with a magnetic disk drive, an optical disk drive, a solid-state device, or an attachment to network storage. In some embodiments, a memory of the databases 104 may be a temporary memory, meaning that a primary purpose of the memory is not long-term storage. Examples of the volatile memories of the databases 104 may include dynamic random access memories (DRAM), static random access memories (SRAM), and other forms of volatile memories known in the art. In some embodiments, the memory of the databases 104 may be configured to store larger amounts of information than volatile memory.

A server 106 is a computing device comprising a processor and non-transitory machine-readable storage capable of executing various tasks and processes described herein. The server 106 is programmed according to an event-driven asynchronous architecture. The event-driven architecture is a software architecture pattern promoting the production, detection, consumption of, and reaction to events. The event is defined as a significant change in state. For example, when a user purchases a product, the product's state changes from "for sale" to "sold". The system architecture may treat the state change as an event whose occurrence can be made known to other applications within the architecture. What is produced, published, propagated, detected or consumed is a (typically asynchronous) message called the event notification, and not the event itself, which is the state change that triggered the message emission. Non-limiting examples of such computing devices may include workstation computers, laptop computers, server computers, laptop computers, and the like. While the system 100 includes a single server 106, in some embodiments, the server 106 may include any number of computing devices operating in a distributed computing environment. It would also be appreciated that although the server 106 is shown in FIG. 1 as being a separate device from a webserver 110, in some embodiments the webserver 110 and the server 106 may be the same device.

The server 106 may generate mortality models, modify the mortality models, and execute the mortality models hosted on a database 104. The mortality model may be generated for each location. In some cases, the mortality model be associated with a set of unique characteristics. The mortality model may correspond to an artificial intelligence model that may include a set of rules utilizing varying values and risk characteristics. The varying values and risk characteristics may be associated with air particulate information of one or more locations. The air particulate information may be associated with air particulate datasets at one or more locations, such as where the user may have worked or lived during the user's lifetime. The air particulate information may be associated with the air particulate datasets at the one or more locations during a predetermined period of time. The predetermined period of time may be any amount of days, weeks, months, or years. If the user lived at a first location for 20 years and a second location for 30 years, the server would retrieve air particulate data from the first location and the second location. The server would also calculate a score that weights the analysis of the particulate data based upon the time spent at each location. The score can also be weighted based upon the age of the user at that location (e.g., a higher weighting for a younger age). The score can then be inputted into the mortality model, which can further learn from the input of this data.

The mortality model may employ statistical tools and artificial intelligence algorithms. The statistical tools may include artificial neural networks and Monte Carlo analysis. The mortality model may define a hierarchy of data elements for describing a health service product. The mortality model may define the data elements that may include data sub-elements. For instance, a country pollutant data element may be a data element that includes city and state wise pollutant data sub-elements. The mortality model may further specify data elements at various places within the hierarchy of the data elements. In some cases, the mortality model can be customized by defining data elements that are specific to different pollutant detection applications. For example, the data elements of the health service product class may have a data element for each country pollutant data detected by each type of pollutant detection applications.

The server 106 may be in communication with pollutant data collectors and/or a third-party server, which monitors and detects pollutant data at various locations (e.g., countries, cities, states, provinces) for a predetermined period of time in real-time. The pollutant data collectors may include sensor devices to monitor and detect pollutant data in real time at various locations. The sensor devices may then store the pollutant data in the database 104. The sensor devices may transmit the pollutant data to the application server 112. Each sensor device may include a processor and a memory. The sensor device may include one or more transceivers. The transceivers may detect broadcasted pollutant information messages from the pollutant detectors. For instance, the transceivers may obtain real-time information associated with the pollutant data and the air particulate data from the pollutant detectors, and then generate and transmit control signals in real-time containing information regarding the pollutant data and the events to the server 106. The control signals may be RF signals. Also, the control signals may contain a unique identification code identifying the sensor devices and/or the pollutant detectors. The unique identification code may include information about a type of the sensor device/pollutant detector, and pollutant information being presented by the sensor device/pollutant detector. The control signals may also include a location identifier identifying the location of installation of the sensor devices and/or the pollutant detectors. For example, the sensor devices and/or the pollutant detectors may be mobile devices, and located in an automobile. In such a case, the control signals may include information regarding all the locations that the automobile has visited. In another example, the sensor devices and/or the pollutant detectors may be static devices, and located in an industrial facility. In such a case, the control signals may include information regarding location data of the industrial facility.

The server 106 upon receiving the air particulate datasets from the pollutant data collectors may then format the air particulate datasets according to a common format and data type. For instance, each pollutant data collector may generate the air particulate datasets based on different formats and data types, and the server 106 upon receiving all the air particulate datasets from all the pollutant data collectors may then standardize and/or format all the air particulate datasets having a different format and a data type according to a common format and data type. Then, the server 106 may calculate one or more pollutant indicators (such as risk indicators) for each location at each time during a predetermined period of time based on the set of air particulate datasets. The server 106 may calculate the pollutant indicators based on the set of air particulate datasets as well as one or more characteristics associated with each location. The characteristics associated with each location may include at least an altitude data of each location and a temperature data of each location. The server 106 may further take into account as an input an activity that caused pollutant in each location while calculating the one or more pollutant indicators for each location. For example, the electricity used in New York has a significantly lower carbon footprint than electricity used in Shanghai because 80% of the electricity provided in New York comes from either atomic or hydro-electric sources whereas 80% of the electricity used in Shanghai comes from coal fired generators. As another example, different countries use different protocols to calculate pollutant values. The server 106 may take into consideration as an input the location when determining how an emission value should be calculated in order to comply with a given protocol. The server 106 may continually receive new set of air particulate datasets from the pollutant data collectors in real-time, and accordingly the server 106 may update the pollutant risk indicators for each location in real-time in accordance with new information contained in the new set of one or more particulate datasets.

In operation, the server 106 may generate and execute the mortality model. The mortality model may have a set of rules utilizing varying values and risk characteristics associated with the air particulate indicators and the pollutant records for each location at each time during a predetermined period of time obtained from the pollutant data collectors. The server 106 may generate the mortality model using the air particulate indicators and the pollutant records obtained from a third-party server. Examples of the air particulate datasets for each location in each country may include, but not limited to, values of sulfur emission and carbon emissions, e.g., carbon dioxide emissions and pollutants, such as greenhouse gasses, that are measured in carbon dioxide emission equivalents, NOx emissions, noise, light, consumer waste, consumer waste pollutant, and any combinations thereof. The server 106 may periodically update the air particulate datasets to an extent that new data points for the set of air particulate datasets are generated. For example, the server 106 may update air particulate record of a particular city using new emission data or by web crawling different database (e.g., emission related databases). Furthermore, for a set of models, the server 106 may execute a model such as a linear model appearing as a linear regression where inputs are data points, as disclosed herein, and are fit to a response variable that indicates a survival time and leaf squares are performed to quantify an error and a gradient is dispensed to optimize a function, and a random survival forest (a collection of decision trees, where a number of trees and a depth of trees is compared and optimized as data changes/updated, such as the set of user records), where a prediction that is output from the combination are input into another cost regression model to get an air particulate related risk score value.

The server 106 may generate the mortality model using the air particulate datasets and multiple user's records. Each of the user records may contain a set of discrete observation values about a particular user, such as what a user risk profile looks like at a certain point in time depending on location of the user at that point in time. The information can be obtained from a set of inputs received from a set of users relating to a specific data point associated with the users, such as a question answered by the user, a service requested by the users, and others. Likewise, each of the user records may contain a survival information, such as numerical data, which varies through time until a death event is recorded for that record. In some embodiments, the set of user records are periodically updated in the database 104 to include survival information for each of the users and to an extent that new data points for the set of user records is received. For example, a user's data record may be updated in the database 104 using new health data (e.g., a new disease diagnoses) or by web crawling different database 104 (e.g., social networking databases or health related databases).

The server 106 may further determine a mortality risk, which is learned from a set of user's health variables and a set of air particulate indicators extracted from the set of complete data, such as the set of user records and the set of air particulate datasets. The server 106 may integrate some of the variables into a mortality risk model. For example, the variables may include at least one of the age and sex of the user, the user's credit rating, the amount of death benefit, the original life expectancy, the premium amount, and certain health specific information, including but not limited to smoker indication, prescription information, and general medical information (e.g., surgeries, treatments, etc.). The server 106 may then use health variables to calculate a value for a health service policy based at least in part on the original life expectancy report and/or the air particulate datasets report associated with the user, adjustments to the life expectancy of the user, and the remaining stream of premiums. The air particulate datasets report may indicate information regarding air particulate values at each location where the user has lived at the time the user was living at that location.

The server 106 may generate and execute a mortality model, which may include various data trees. The server 106 may generate an average across the data trees, where conditional dependencies can be built after running through a tree, scan values of variables, and then scan the values of user records that are flagged as alive or dead, and then runs through a subsequent tree; and then uses a new variable to split the prior tree into the sub-tree. Consequently, the user records can be grouped according to likelihood of mortality by a variable (e.g., age) because age is a good indicator of alive/dead in the dataset, and then a next variable (e.g. air particulate and other pollutant data of user previous and current location of residence) can be used to identify when the next variable becomes a good indicator of breaking group into alive or dead; automatically breaks the group up using a log-rank test to determine whether there is a good indicator to break up groups; as preferred to choose a value that maximizes the log rank score for the survival score to do a split. This may be done via running through datasets of clients or publicly available or proprietary databases (LexisNexis queries) for labeled dataset.

For each tree built by the server 106, a variable is chosen from a subset of all variables available that maximizes a particular test statistic that summarizes survival between at least two groups. For example, if "pollutant data at current and past locations of the user" is chosen as a splitting variable/threshold, then the pollutant data splits the set of user records set into two groups: one group that has a value of pollutant data less than that threshold and another one that has one greater. The pollutant data is chosen such that a survival characteristic of those two groups, i.e., a difference between the two groups, is maximized. This difference is quantified through a long-range statistics that is computed via comparing a Kaplan-Meier estimator between a survival curves of the two groups. Resultantly, as the set of user records is updated, a search is performed over all different combinations of the number of trees and the depth of trees to find a combination that maximizes a particular performance metric that is being used for quantification. Since each tree is going to maximize the metric, but an exact number of how many trees and the depth of trees is unknown, various iterations/traversals/searches are performed, i.e., a vast search (end by end metric or M by M) over all different combinations and you choose a combination that maximizes a particular performance statistic, such as concordance (a probability of ranking a pair of observations according to which one dies first or which, you know, which one is the most likely to die first). For example, for two records of the set of user records, one of two records corresponds to a deceased individual and the other of the two records corresponds to somebody that is still living, then the dead individual may be ranked first and the still living individual may be second. For example, same methodology may apply if, for two records of the set of user records, one individual or both individuals are deceased, then the two records are ranked according to which one deceased first. A fraction of time this is performed correctly corresponds to a concordance which can be interpreted as a probability of selected the first deceased correctly. Note that although a tree can be maximized for a particular metric, such as under ten thousand iterations in about twenty-four hours, in some implementations, multiple metrics can be maximized for.

The intense processing (e.g., requiring a high amount of computing power) cannot be manually performed. Even if a health-related variable could be manually processed in isolation (e.g. determine how the risk variable varies with a risk, such as with a pollutant based mortality risk, and then a point value is subjectively assigned to that based on how important that subjectively is and then move to a next point and so on), in contrast, various data structure methods, as disclosed herein, such as tree-based processing, a set of conditional probabilities or conditional risks is generated that is based on hundreds of interactions between different types of variables that are observed on a particular individual at a particular point in time, as memorialized in that user record. When performed by conventional computing devices and using the conventional brute force method (e.g., calculating each permutation and each variable separately and aggregating the big data of the air particulate datasets), the above-mentioned calculations are extremely time-consuming and require a very high computing power. However, using the methods and the computer infrastructure, presented herein, may reduce the computing power needed or time consumed to achieve the same and/or better results.

Stated differently, historical health-related assessments have looked at each variable independently of all others and assigned a score or a weighting to that variable. Then, the next variable is independently examined and so on until all relevant data points have been exhausted. Then, all the examined data points are summed up, i.e., points that are assigned for falling in different ranges for each one of those variables. In contrast, a holistic score is automatically generated that learns what kinds of dependencies or interactions exist amongst those variables and how they correlate with risk. For example, in context of risk assessment, traditionally, assuming one is trying to minimize points to correspond to lower risk, less points are assigned to user records/profiles for older users than for users of any age who have lived in high pollutant areas. However, in a mortality model as applied to a particular user record, as disclosed herein, upon examination of each of such variables, such as age and current and past location pollutant records, and upon examination of a distribution of having a low age and a low pollutant record, a risk value may be determined that for that particular user record the risk value may actually be low.

The server 106 may generate and execute a pricing model module. The pricing model module is a software program associated with one or more pricing parameters of a health-related service. The pricing parameters may include one or more factors used to incorporate geographical, demographic and other data into the rating and pricing of the health-related service. One or more templates of the pricing model module may be composed by using historical data from previous transactions of the health-related services. The templates have their parameter values set as default values based on the historical data. The execution of the pricing model module may provide a recommendation for health-related service to a user interacting with the server 106 via the webserver 110. The recommendation may include a price of the health-related service and a time-period for the health-related service. In operation, the server 106 may compare the risk value with a predetermined threshold. When the risk value satisfies the predetermined threshold, the server 106 may then execute the pricing model module. Prior to execution, the server 106 may provide several inputs into the pricing model module. One input may include the risk value. Another input may include information associated with the air particulate datasets and the pollutant indicators stored in the database 104. Yet another input may include information associated with a questionnaire. For instance, the user may be provided with the questionnaire on the client device 108. The questionnaire may include questions related to age and income of the user. The user may submit answers to all questions within the questionnaire. The server 106 may extract information from the completed questionnaire, and provide as an input to the pricing model module. Upon submitting all the inputs to the pricing model module, the server 106 may execute the pricing model module. On execution, the pricing model module may produce a numerical value. The numerical value maybe included in a list of numerical values stored in the database 104. Each numerical value represents a type of the health-related service and a price range for the health-related service.

The server 106 may use the numerical value along with the information associated with the user to generate an output. The output may include a recommendation of one or more health-related services for the user. The output may further include a price for each health-related service. The server 106 may dynamically update the user interface of the client device 108 of the user with the recommendation. The recommendation may include information associated with the one or more health-related services. The recommendation to the user further include specific details of each health-related service such as monthly price or premiums. While the server 106 may recommend the one or more health-related services to the user, the decision of whether to accept or reject the recommendation is solely user decision. For instance, the user may decide which option among the one or more health-related services the user wants to use. Once the user via the client device 108 selects a particular health-related service, the server 106 takes the user from the recommendation plan into the necessary service fulfillment systems on the client device 108 through the use of web links where the user can take the necessary action(s) in order to purchase the particular health-related service suggested by the recommendation. The server 106 may update the user interface of the client device 108 with the recommendations through the formulation of a service recommendation that includes health services product level details, which is accessible by the user.

Any servers disclosed herein can be hardware-based and/or software-based. Each of the servers is and/or is hosted on, whether directly and/or indirectly, a server computer, whether stationary or mobile, such as a kiosk, a workstation, a vehicle, whether land, marine, or aerial, a desktop, a laptop, a tablet, a mobile phone, a mainframe, a supercomputer, a server farm, and so forth. The server computer can comprise another computer system and/or a cloud-computing network. The server computer can run any type of an OS, such as MacOS, Windows, Android, Unix, Linux, and/or others. The server computer can include and/or be coupled to, whether directly and/or indirectly, an input device, such as a mouse, a keyboard, a touchscreen, a biometric reader, a clicker, a microphone, or any other suitable input device. The server computer can include and/or be coupled to, whether directly and/or indirectly, an output device, such as a display, a speaker, a printer, or any other suitable output device. In some embodiments, the input device and the output device can be embodied in one unit, such as a touch-enabled display, which can be haptic. Each of the servers can employ load-balancing technologies and/or failover technologies for operational efficiency, continuity, and/or redundancy. Each of the servers can be task-dedicated. At least two of the servers can be a single server.

The client devices 108 disclosed herein can be hardware-based and/or software-based. Each of the client devices 108 is and/or is hosted on, whether directly and/or indirectly, a client computer, whether stationary or mobile, such as a terminal, a kiosk, a workstation, a vehicle, whether land, marine, or aerial, a desktop, a laptop, a tablet, a mobile phone, a mainframe, a supercomputer, a server farm, and so forth. The client device 108 can comprise another computer system and/or cloud computing network. The client device 108 can run any type of an OS, such as MacOS, Windows, Android, UNIX, Linux, and/or others. The client device 108 can include and/or be coupled to an input device, such as a mouse, a keyboard, a camera, an accelerometer, a touchscreen, a biometric reader, a clicker, a microphone, or any other suitable input device. The client device 108 can include and/or be coupled to an output device, such as a display, a speaker, a joystick, a printer, or any other suitable output device. In some embodiments, the input device and the output device can be embodied in one unit, such as a touch-enabled display.

Any strings/symbols disclosed herein can be in any human or machine language in any alphanumeric font or via any pictorial, symbolic, or sound representation, such as a string, an icon, a banner, an audio, a video, a vibration, or a photo. Also, note that if any strings/symbols/identifiers disclosed herein are improperly formatted, then the application server 112 may format into an appropriate format. For example, if the application server 112 receives a string/symbol in a first format, then the application server 112 can convert the string/symbol from the first format into a second format, such as for data structure or processor compatibility or computational efficiency. For the example, the first format can be in a first character-encoding scheme and the second format can be in a second character-encoding scheme. For example, the first format can an archive or zipped file and the second format can be un-archived or unzipped file.

An input can be in a natural language form, such as in a sentence, sound, or image, where such input can be subsequently processed via the application server 112 implementing a natural language processing algorithms, such as based on statistical model machine learning. For example, such algorithms can involve automatic summarization, co-reference resolution, discourse analysis, machine translation, morphological segmentation, named entity recognition (NER), native language identification, natural language generation, natural language understanding, OCR, part-of-speech tagging, parsing, question answering, relationship extraction, sentence breaking, sentiment analysis, speech recognition, speech segmentation, stemming, topic segmentation and recognition, word segmentation, word sense disambiguation, or others.

Figure 2:
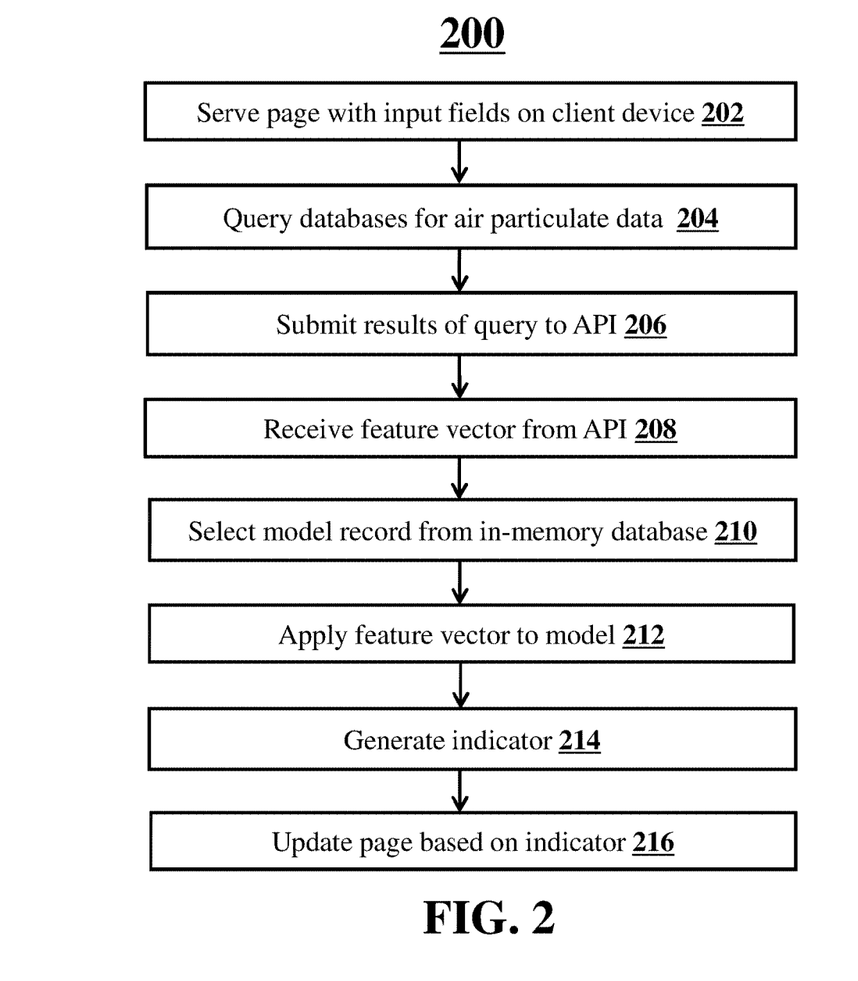
FIG. 2 shows execution of a method for execution of a mortality model, according to an embodiment.

FIG. 2 shows execution of a method 200 for execution of a mortality model. FIG. 3 will be explained in conjunction to FIG. 1. The method 200 shown in FIG. 2 comprises execution steps 202, 204, 206, 208, 210, 212, 214, and 216. However, it should be appreciated that other embodiments may comprise additional or alternative execution steps, or may omit one or more steps altogether. It should also be appreciated that other embodiments may perform certain execution steps in a different order; steps may also be performed simultaneously or near-simultaneously with one another. In addition, the method 200 of FIG. 2 is described as being executed by a single server computer in this embodiment. The single server computer is programmed according to an event-driven asynchronous architecture. However, one having skill in the art will appreciate that, in some embodiments, steps may be executed by any number of computing devices operating in a distributed computing environment. In some cases, a computer executing one or more steps may be programmed to execute various other, unrelated features, where such computer does not need to be operating strictly as the server computer described herein.

In step 202, a server may serve a network page with a set of input fields to a client computing device over a network. For example, a network page may include a form or a questionnaire for completion by a user of the client computing device where the form includes a plurality of graphical elements, such as text fields, buttons, sliders, checkboxes, dropdown menus, or others, for interaction with the user, and where the form is or will be associated with a profile corresponding to the user. For example, the form can intake user information for a provision of a health-related service to the user. The server may then receive an input from an input field on the page on the client computing device. For example, the input can include an alphabetic string, a numeric string, or a binary value, where the input is received as the input field is being populated or after being submitted in response to a user activation, such as pressing a button or activating a hyperlink on the page.

The server may receive a request from an input field of the network page served to the client computing device over a network. The request may include an input from the input field. The server may then query a risk score value associated with the user of the request from an application server. The application server may then execute a first process to obtain the risk score value. During the execution of the technique, the application server execute a second process to determine the risk score value. The risk score value is based on the input and associated with the profile corresponding for the user. The risk score value enables a determination whether the provision of the health-related service to the user is feasible.

The second process may be executed during the first process, which itself is performed during the execution of the method 200. Since the method 200 is executed during an intake of the user information for the provision of the service to the user, the first process and the second process may be performed during the method 200 and therefore can be performed in parallel or in real-time as the input fields are being populated on the page on the client computing device, which may include the form. Therefore, such processing minimizes computational repetition based on verification or validation of the input, while minimizing a delay in verification or validation of the input, as disclosed herein. For example, the method 200, including a first process and a second process, which can be performed under a very short period of time, for instance, one minute, such as under 45 seconds, under 30 seconds, under 15 seconds, under 10 seconds, or under 5 seconds.

In step 204, a server may execute a first process during which an application server may query a set of databases over a network via a network server. The application server may include a multicore processor for parallel processing operations during querying of the multiple databases. The query may include questions for obtaining the air particulate data associated with at least one location record of the user for a period of time at which the user is associated with the location of the location record. For example, the request of the user may indicate that the user lived for 1 year in China between the year 2000 and 2001, and 1 year in Kenya between the year 2004 and 2006. Based on the information within the request, the generated query may include questions for obtaining the air particulate data for the China between the year 2000 and 2001, and for Kenya between the year 2004 and 2006.

The databases store pollutant data such as a set of air particulate datasets for one or more countries like China, USA, Kenya, etc. For instance, the database may store a large amount of pollutant data obtained from approximately 42,000 pollutant data collectors all across China over a period of 40 years. The pollutant data collectors may be installed in air monitoring stations to detect air pollution and collect air pollutant data in real-time. The pollutant data collectors may include sensor devices to detect air pollution and collect air pollutant data in real-time. The pollutant data collectors may report big air particulate datasets having concentrations in (mg/m3) for major pollutants such as sulfur dioxide ($SO_2$), nitrogen dioxide ($NO_2$), and particulate matter (PM10, particles with a diameter of 10 microns or less) in real-time, hourly basis, and these datasets are then stored in the database. All particulate datasets reported by the pollutant data collectors may include location identifiers. The location identifier associated with each air particulate dataset may indicate information of a location where the pollutant data collector detected the air pollution.

In step 206, an application server may receive a plurality of results from the databases over a network via a network server. The results may include information associated with the air particulate data associated with the location record of the user for the period of time at which the user is associated with the location of the location record. The application server may submit the results to an application-programming interface (API) hosted on the application server. The results may include alphanumeric data, binary data, image data, audio data, or others corresponding to big air particulate datasets associated with one or more locations of the user. The application server may also transmit other information associated with the request of the user to the AP1.

In step 208, an application server may receive a feature vector from the API based on the processing of information within the results and/or the request of the user. The feature vector is associated with the information in the profile of the user. For example, the feature vector is a multi-dimensional vector of numerical features that represent at least one attribute associated with the profile of the user. Each attribute may be associated with the information corresponding to pollution datasets in at least one location of the list of locations where the user has previously stayed. The information corresponding to the pollution datasets is for a time period the user stayed at the at least one location.

In step 210, an application server communicably interfaces with a database server, where the database server hosts a DBMS and an in-memory database managed via the DBMS. The in-memory database stores a set of model records, where each of the model records stores a field containing an artificial intelligence model comprising machine learning algorithms. Additionally or alternatively, the record is the artificial intelligence model. Additionally or alternatively, a set of records define the artificial intelligence model when the set of records is aggregated, such as via the DBMS or the application server, and then processed, such as via the DBMS or the application server, such that the artificial intelligence model is created or formed thereby. In some cases, a different artificial intelligence model may be there to evaluate air particulate data of each country. For example, a first artificial intelligence model may have a neural network that is associated with the air particulate data of a first country, and a second artificial intelligence model may have a neural network that is associated with the air particulate data of a second country.

The application server may select a model record from a set of model records via the DBMS based on the feature vector. The application server may then retrieve the artificial intelligence model therefrom for use in an application running on the application server. For example, when the feature vector is associated with a characteristic of the profile of the user where the characteristic includes a number of countries where the user has lived, then the application server may retrieve the artificial intelligence model based on the corresponding value of the feature vector. The application server may then insert the artificial intelligence model into the application for processing for use with the feature vector. The model record may be selected via the application based on the application analyzing the feature vector, and correspondingly determining, based on a content or structure of the feature vector, which model record of the set of model records contains the artificial intelligence model suitable or appropriate for that feature vector. For example, the analysis can generate a set of parameters based on which the set of model records is searched to identify a suitable or appropriate artificial intelligence model, if any.

In step 212, an application server may submit the feature vector into the artificial intelligence model, which is being executed on the application server. The artificial intelligence model may correspond to a mortality model configured to determine information associated with the mortality of the users. The mortality model may user statistical tools and artificial intelligence algorithms. The statistical tools may include artificial neural networks and Monte Carlo analysis. In operation, the application server applies the feature vector as an input to the artificial intelligence model. The artificial intelligence model then processes and analyzes all information corresponding to the feature vector. The application server may also submit other data associated with the request as an input to the artificial intelligence model. The artificial intelligence model may also process and analyze the other data along with the information corresponding to the feature vector.

In step 214, in response to all the received inputs, the artificial intelligence model may generate an indicator. The indicator may include a graphical representation of a risk score value, which is a numeric value. To generate the risk score value, the artificial intelligence model incorporates information associated with the air particulate data from each location associated with the user for each period of time each location is associated with the user. The information may also include characteristics associated with each location corresponding to the set of air particulate datasets. The characteristics may include at least an altitude of each location and a temperature value at each location. After generating the risk score value, the artificial intelligence model may transmit the risk score value to an application server. The application server on receiving the risk score value from the artificial intelligence model may transmit the risk score value to a server. The application server may also store the risk score value in a database.

The artificial intelligence model may generate an updated risk score value based on updated inputs. For instance, when updated information associated with the air particulate datasets from one or more locations is obtained from the pollutant data collectors, then inputs to the artificial intelligence model are updated. Accordingly, based on the updated inputs, the artificial intelligence model may generate the updated risk score value.

In step 216, a server may receive a risk score value from an application server. The server may then dynamically updates the page on the client computing device over a network based on the risk score value. The updates to the page may include information, which may indicate whether the request of the user is accepted or declined. For example, the updated network page may displays a status of eligibility for availing the health-related services. The status of eligibility may include an acceptance message or a non-acceptance message regarding availability of the health-related services.

In some cases, the server may compare the risk score value with a predetermined threshold. When the risk score value satisfies the predetermined threshold, the server may execute a pricing model module using various inputs. The inputs may include the risk score value and other attributes associated with the user such as age of the user. The pricing model module may be a software module (e.g., non-transitory computer readable instructions for execution by a processor) configured to determine a price for the health-related service available to the user. The pricing model module may be hosted on the server and executed by the server, or the pricing model module may be hosted on a different computer and executed upon receiving instructions when the indicator satisfies a threshold. The pricing model module can receive the inputs and calculate a value, which may represent a category (e.g., class) associated with a price or the value may be a price. Once the pricing model module is executed, the server or other computer that executes the pricing model module causes the page to dynamically update on the client computing device with the price for the available health-related service. For example, the result of the execute of the pricing model module can cause a webserver or the application server to present an updated or new page for display on a browser or other user interface on the client computing device.

Figure 3:
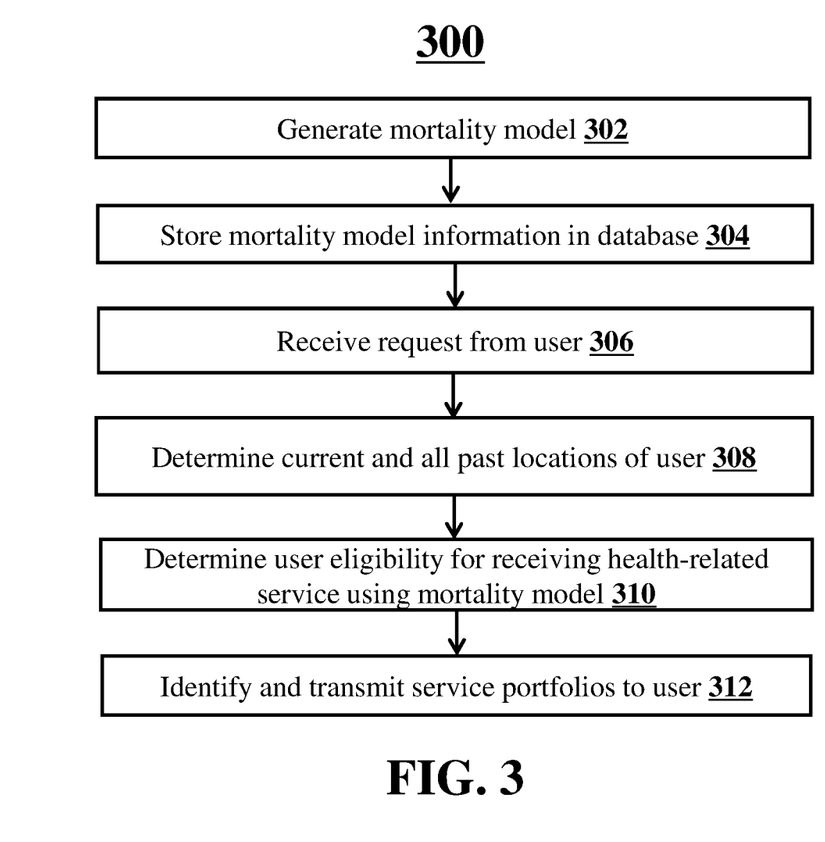
FIG. 3 shows execution of a method for generation and execution of a mortality model, according to an embodiment.

FIG. 3 shows execution of a method 300 for generation and execution of a mortality model. FIG. 3 will be explained in conjunction to FIG. 1 and FIG. 2. The method 300 shown in FIG. 3 comprises execution steps 302, 304, 306, 308, 310, and 312. However, it should be appreciated that other embodiments may comprise additional or alternative execution steps, or may omit one or more steps altogether. It should also be appreciated that other embodiments may perform certain execution steps in a different order; steps may also be performed simultaneously or near-simultaneously with one another. In addition, the method 300 of FIG. 3 is described as being executed by a single server computer in this embodiment. However, one having skill in the art will appreciate that, in some embodiments, steps may be executed by any number of computing devices operating in a distributed computing environment. In some cases, a computer executing one or more steps may be programmed to execute various other, unrelated features, where such computer does not need to be operating strictly as the server computer described herein.

In step 302, a server computer receives a set of one or more air particulate datasets containing a location identifier from one or more pollutant data collectors. The one or more pollutant data collectors are configured to monitor and detect pollutant information for one or more locations for a first predetermined period of time. Each of the one or more pollutant data collectors may include one or more sensor devices such transceivers that are configured to generate the set of one or more air particulate datasets containing information about air particulate data detected by the one or more sensor devices. The one or more sensor devices may detect broadcasted pollutant information messages from one or more pollutant detectors, and then generate and transmit one or more control signals containing information regarding the air particulate data based on the broadcasted pollutant information messages to the one or more pollutant data collectors. The information about air particulate data may include a type of pollutant event, a location of pollutant event, a date of pollutant event, and a carbon footprint value because of the pollutant event. In some embodiments, the one or more control signals may be RF signals. The one or more control signals may include a unique identification code identifying the one or more sensor devices. In some embodiments, the one or more control signals may include a location identifier identifying the location of the one or more sensor devices. For example, the one or more sensor devices may be mobile devices and located in an automobile. In such as a case, the one or more control signals may include location information of all the places that the automobile has been. In another example, the one or more sensor devices may be static devices and located in an industrial facility. In such a case, the one or more control signals may include location information of the industrial facility.

The server computer on receiving the set of one or more air particulate datasets containing the location identifier from the one or more pollutant data collectors may then format all the air particulate datasets according to a common format and data type. Then, the server computer may be configured to calculate one or more pollutant risk indicators for each location at a particular time during the predetermined period of time based on the set of one or more pollutant data records. In some embodiments, in order to calculate the one or more pollutant risk indicators, the server computer may also use one or more characteristics associated with each location such as an altitude of each location and a temperature of each location in addition to the one or more pollutant risk indicators for each location. In some embodiments, the server computer may be configured to periodically update the one or more pollutant risk indicators for each location as new set of one or more air particulate datasets is received by the server computer from the one or more pollutant data collectors.

The server computer may then be configured to generate a risk based mortality model based on the one or more pollutant risk indicators for each location at each time during the predetermined period of time. The risk based mortality model may include one or more set of rules utilizing varying values and risk characteristics associated with the one or more pollutant risk indicators for each location at the particular time during the predetermined period of time. In some embodiments, the risk based mortality model may utilize one or more statistical tools and one or more artificial intelligence algorithms. The one or more statistical tools comprises artificial neural networks and Monte Carlo analysis. Upon generation of the risk based mortality model, the server computer may be configured to store the risk based mortality model in a database, in step 304.

In step 306, a server computer may receive information associated with one or more requests from one or more user computing devices. The one or more user client computing devices may be operated by one or more users. The one or more requests of the one or more users may be associated with an application to receive one or more health-related services.

In step 308, a server computer may be configured to query the database to receive a set of datasets corresponding to locations of one or more users. Each dataset corresponding to the one or more users may include data associated with each user comprising at least each user's location data for a predetermined period of time. For example, the dataset may include location data associated to all the past as well as current residence and work location of the users.

Upon querying the database, in a first scenario, the server computer may receive the set of datasets comprising each user's location data for the predetermined period of time from the database. In a second scenario, when the computer does not receive from the database the set of datasets comprising each user's location data for the second pre-defined period of time, the server computer may transmit a web link to a secure webpage having a request with an instruction to populate missing location information for the pre-defined period of time to the one or more user computing devices. The server computer may then receive data for the information from the one or more user computing devices, and then generate and/or update a user profile for each of the one or more users with received information and other information already present in the database.

In step 310, a server computer may be configured to execute the risk model on the user profile information and the information associated with the one or more requests comprising the location data for the predetermined period of time to determine the eligibility of the one or more users to receive the one or more services. In some embodiments, the eligibility of the one or more users to receive the one or more services may also be determined by the server computer based on the pollutant risk indicator for each location where the one or more users have lived during the predetermined period of time.

In step 312, a server computer may be configured to display a status of eligibility message for receiving the one or more services on a graphical user interface of the one or more user computing devices. The status of eligibility message may include an acceptance message or a non-acceptance message. The non-acceptance message may include one or more instructions for the user to submit additional information in order to reprocess the user's request to avail the one or more services. The acceptance message may include information regarding eligible service portfolio models to the user based on the request of the user.

Example

A user operating a client computing device may access a web application. The web application may display a form related to a request for a health-related service. The user may electronically input responses to the form using various input components displayed by the web application. The form may include a field to submit information of all locations where the user has previously lived. While answering questions in the form, the user may submit a name of each location where the user has previously stayed, such as, Shanghai, China; Mexico City; Seoul, Korea, and New York, NY. The user may also submit dates of stay at each location, such as, from 1998-2009 in Shanghai, China; from 2011-2012 in Mexico City; from 2012-2014 in Seoul, Korea, and from 2009-2011 and 2014 until present in New York, NY. Additional data inputted in the form may also include personal or demographic information of the user, such as address, age, credit score, and health information.

The web application may transmit the answers inputted by the user to a database. The server may retrieve the answers from the database. The server may then parse the answers to extract information. The server may create a user profile of the user using the information. The server may query a database to obtain information associated with air particulate datasets for all the locations during the period of the stay of the user. For instance, the server may retrieve, from a database, information associated with the air particulate datasets in Shanghai, China from 1998-2009; in Mexico City from 2011-2012; in Seoul, Korea from 2012-2014, and in New York, NY from 2009-2011 and 2014 until present.

The server may generate a feature vector corresponding to the user profile. The feature vector is an n-dimensional vector of features that represent essential characteristics of information associated with the user. The characteristics may include air particulate data corresponding to all the locations during the period of the stay of the user. The server may select an AI motility model based on the feature vector. For instance, the server may select the AI mortality model that is trained with pollution datasets of China as the longest period of stay of the user was in China, and China is the most polluted country among all the countries where the user had lived. The server may submit the feature vector, the information associated with the user profile, and the air particulate datasets as an input to the artificial intelligence model. In response to all the received inputs, upon execution, the artificial intelligence model may generate a numeric value. The artificial intelligence model may then transmit the numeric value to the server. Based on the numeric value, the server may determine a status of the request of the user. For instance, the server may determine a status of eligibility for the user to avail the health-related service based on the numeric value. The status of eligibility may include an acceptance message or a non-acceptance message regarding the availability of the health-related service. The server may display the status of eligibility on the client computing device.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present subject matter.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the subject matter. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present subject matter. Various modifications to these embodiments will be readily apparent to those skilled in the art, and the generic principles defined herein may be applied to other embodiments without departing from the spirit or scope of the subject matter. Thus, the present subject matter is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A server-implemented method comprising:

receiving, by a server programmed according to an event-driven asynchronous architecture, from a client computing device operated by a user, a request from an input field of a network page served to the client computing device, the request comprising one or more attributes of the user, a list of locations, and a time period during which the user has been associated with each location;

in response to receiving the request, querying, by the server, an application server to receive a set of air particulate datasets corresponding to the user, wherein the set of air particulate datasets comprises air particulate data associated with at least one location within the list of locations and a corresponding time period;

generating, by the server, a multi-dimensional feature vector where each dimension corresponds to a location from the list of locations and the corresponding time period at which the user is associated with the location;

selecting, by the server, based on the list of locations, from a plurality of artificial intelligence models, one or more artificial intelligence models suitable for the multi-dimensional feature vector and respectively corresponding to each location in the list of locations, each artificial intelligence model having a neural network that is trained on multi-dimensional feature vectors corresponding to users, information associated with user profiles of the users, and air particulate data corresponding to each location in the list of locations, each of the one or more artificial intelligence models trained using a respective dataset corresponding to a respective location of the list of locations, the one or more artificial intelligence models associated with a set of rules corresponding to a plurality of locations;

executing, by the server, the one or more artificial intelligence models based on the multi-dimensional feature vector and the set of air particulate datasets;

generating, by the server executing the one or more artificial intelligence models, a score by applying the set of rules to an output of each of the one or more artificial intelligence models; and executing by the server, a pricing module based on the user profile of the user and the score, that results in providing a health-related service recommendation for the user and a price range for the health-related service.

2. The server-implemented method according to claim 1, wherein each dataset of the set of air particulate datasets contains a location identifier from one or more pollutant data collectors configured to monitor and detect air particulate data for one or more locations.

3. The server-implemented method according to claim 2, wherein each of the one or more pollutant data collectors comprises one or more sensor devices configured to generate the set of air particulate datasets containing information corresponding to air particulate data detected by the one or more sensor devices, wherein the one or more pollutant data collectors store the set of air particulate datasets in the one or more databases.

4. The server-implemented method according to claim 3, wherein the one or more sensor devices transmits one or more control signals containing information regarding the air particulate data to the one or more pollutant data collectors, and wherein the one or more control signals are RF signals.

5. The server-implemented method according to claim 4, wherein the one or more control signals comprises a unique identification code identifying the one or more sensor devices and a location identifier identifying the location of the one or more sensor devices.

6. The server-implemented method according to claim 2, wherein the one or more pollutant data collectors are mobile collectors and located in an automobile.

7. The server-implemented method according to claim 2, wherein the one or more pollutant data collectors are static collectors and located in an industrial facility.

8. The server-implemented method according to claim 1, wherein the one or more artificial intelligence models are further configured to generate the score for the set of air particulate datasets based at least in accordance with one or more characteristics associated with each location corresponding to the set of air particulate datasets, wherein the one or more characteristics comprises at least an altitude of each location and a temperature value at each location.

9. The server-implemented method according to claim 1, wherein a dynamically updated network page to the client computing device based on the score displays a status of eligibility for availing one or more health-related services, and wherein the status of eligibility comprises an acceptance message or a non-acceptance message regarding availability of the one or health-related services.

10. The method of claim 1, further comprising updating, by the server, the one or more artificial intelligence models based on the score.

11. A system comprising:
a network;
a client computing device operated by a user; and
a server programmed according to an event-driven asynchronous architecture, wherein the server is configured to:
receive from the client computing device a request from an input field of a network page served to the client computing device, the request comprising one or more attributes of the user, a list of locations, and a time period during which the user has been associated with each location;
query an application server to receive a set of air particulate datasets corresponding to the user, wherein the set of air particulate datasets comprises air particulate data associated with at least one location within the list of locations and a corresponding time period;
generate a multi-dimensional feature vector where each dimension corresponds to a location from the list of locations and the corresponding time period at which the user is associated with the location;
select, based on the list of locations, from a plurality of artificial intelligence models, one or more artificial intelligence models suitable for the multi-dimensional feature vector and respectively corresponding to each location of the list of locations, each artificial intelligence model having a neural network that is trained on multi-dimensional feature vectors corresponding to users, information associated with user profiles of the users, and air particulate data corresponding to each location in the list of locations, each of the one or more artificial intelligence models trained using a respective dataset corresponding to a respective location of the list of locations, the one or more artificial intelligence models associated with a set of rules corresponding to a plurality of locations;
execute the one or more artificial intelligence models based on the multi-dimensional feature vector and the set of air particulate datasets;
generate a score by applying the set of rules to an output of each of the one or more artificial intelligence models; and
execute a pricing module based on the user profile of the user and the score, that results in providing a health-related service recommendation for the user and a price range for the health-related service.

12. The system according to claim 11, wherein each dataset of the set of air particulate datasets contains a location identifier from one or more pollutant data collectors configured to monitor and detect air particulate data for one or more locations.

13. The system according to claim 12, wherein each of the one or more pollutant data collectors comprises one or more sensor devices configured to generate the set of air particulate datasets containing information corresponding to air particulate data detected by the one or more sensor devices, wherein the one or more pollutant data collectors store the set of air particulate datasets in the one or more databases.

14. The system according to claim 13, wherein the one or more sensor devices transmits one or more control signals containing information regarding the air particulate data to the one or more pollutant data collectors, and wherein the one or more control signals are RF signals.

15. The system according to claim 14, wherein the one or more control signals comprises a unique identification code identifying the one or more sensor devices and a location identifier identifying the location of the one or more sensor devices.

16. The system according to claim 12, wherein the one or more pollutant data collectors are mobile collectors and located in an automobile.

17. The system according to claim 12, wherein the one or more pollutant data collectors are static collectors and located in an industrial facility.

18. The system according to claim 11, wherein the one or more artificial intelligence models are further configured to generate the score for the set of air particulate datasets based at least in accordance with one or more characteristics associated with each location corresponding to the set of air particulate datasets, wherein the one or more characteristics comprises at least an altitude of each location and a temperature value at each location.

19. The system according to claim 11, wherein a dynamically updated network page served to the client computing device displays a status of eligibility for availing one or more health-related services, and wherein the status of eligibility comprises an acceptance message or a non-acceptance message regarding availability of the one or health-related services.

20. The system of claim 11, wherein the server is further configured to update the one or more artificial intelligence models based on the score.

* * * * *